(12) United States Patent
Arnholt et al.

(10) Patent No.: US 8,565,893 B2
(45) Date of Patent: *Oct. 22, 2013

(54) IMPLANTABLE MEDICAL LEAD HAVING REDUCED DIMENSION TUBING TRANSITION

(71) Applicant: Cardiac Pacemakers, Inc., St. Paul, MN (US)

(72) Inventors: Devon N. Arnholt, Shoreview, MN (US); Douglas D. Pagoria, Forest Lake, MN (US); Raymond D. Gessler, Roberts, WI (US); Duane T. Meyer, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,641

(22) Filed: May 6, 2013

(65) Prior Publication Data

US 2013/0245737 A1    Sep. 19, 2013

Related U.S. Application Data

(63) Continuation of application No. 13/526,071, filed on Jun. 18, 2012, now Pat. No. 8,442,648, which is a continuation of application No. 12/534,114, filed on Aug. 1, 2009, now Pat. No. 8,219,209.

(60) Provisional application No. 61/089,330, filed on Aug. 15, 2008.

(51) Int. Cl.
*A61N 1/00* (2006.01)

(52) U.S. Cl.
USPC .......................................... 607/115

(58) Field of Classification Search
USPC .......................... 607/115, 120, 122
See application file for complete search history.

(56) References Cited

U.S. PATENT DOCUMENTS

| | | |
|---|---|---|
| 3,474,791 A | 10/1969 | Bentov |
| 4,280,511 A | 7/1981 | O'Neill |
| 4,379,462 A | 4/1983 | Borkan et al. |
| 4,381,014 A | 4/1983 | Sandstrom et al. |
| 4,484,586 A | 11/1984 | McMickle et al. |
| 4,573,481 A | 3/1986 | Bullara |
| 4,592,372 A | 6/1986 | Beranek |
| 4,628,934 A | 12/1986 | Pohndorf et al. |
| 4,643,202 A | 2/1987 | Roche |
| 4,711,027 A | 12/1987 | Harris |
| 4,721,115 A | 1/1988 | Owens |
| 4,934,049 A | 6/1990 | Kiekhafer et al. |
| 5,007,435 A | 4/1991 | Doan et al. |
| 5,016,646 A | 5/1991 | Gotthardt et al. |
| 5,016,808 A | 5/1991 | Heil, Jr. et al. |

(Continued)

*Primary Examiner* — Robert N Wieland
(74) *Attorney, Agent, or Firm* — Faegre Baker Daniels LLP (57) ABSTRACT

Lead body designs for forming a fluid tight seal between a multilumen tube and other portions of a lead body are provided. One lead body design has a multilumen tube having a first portion defining a first number of lumens and a second reduced dimension portion defining a second number of lumens, the second number of lumens being smaller than the first number of lumens. The reduced dimension portion is attached to a distal tip portion of the lead body, forming a fluid tight passageway through the multilumen tube to the distal tip portion. Also provided are methods for forming such multilumen tubes and incorporating such multilumen tubes into a lead body.

20 Claims, 4 Drawing Sheets

(56) References Cited

U.S. PATENT DOCUMENTS

| | | |
|---|---|---|
| 5,017,740 A | 5/1991 | Honkomp et al. |
| 5,061,273 A | 10/1991 | Yock |
| 5,076,270 A | 12/1991 | Stutz, Jr. |
| 5,115,818 A | 5/1992 | Holleman et al. |
| 5,170,802 A | 12/1992 | Mehra |
| 5,217,027 A | 6/1993 | Hermens |
| 5,224,491 A | 7/1993 | Mehra |
| 5,231,996 A | 8/1993 | Bardy et al. |
| 5,350,419 A | 9/1994 | Bendel et al. |
| 5,363,861 A | 11/1994 | Edwards et al. |
| 5,368,564 A | 11/1994 | Savage |
| 5,387,233 A | 2/1995 | Alferness et al. |
| 5,423,865 A | 6/1995 | Bowald et al. |
| 5,431,683 A | 7/1995 | Bowald et al. |
| 5,458,629 A | 10/1995 | Baudino et al. |
| 5,466,253 A | 11/1995 | Doan |
| 5,476,498 A | 12/1995 | Ayers |
| 5,483,022 A | 1/1996 | Mar |
| 5,522,872 A | 6/1996 | Hoff |
| 5,545,203 A | 8/1996 | Doan |
| 5,549,642 A | 8/1996 | Min et al. |
| 5,555,883 A | 9/1996 | Avitall |
| 5,649,974 A | 7/1997 | Nelson et al. |
| 5,676,694 A | 10/1997 | Boser et al. |
| 5,741,319 A | 4/1998 | Woloszko et al. |
| 5,766,527 A | 6/1998 | Schildgen et al. |
| 5,792,217 A | 8/1998 | Camps et al. |
| 5,796,044 A | 8/1998 | Cobian et al. |
| 5,823,955 A | 10/1998 | Kuck et al. |
| 5,845,396 A | 12/1998 | Altman et al. |
| 5,853,652 A | 12/1998 | Schildgen et al. |
| 5,871,531 A | 2/1999 | Struble |
| 5,954,759 A | 9/1999 | Swoyer et al. |
| 5,957,966 A | 9/1999 | Schroeppel et al. |
| 6,047,217 A | 4/2000 | Uhrberg |
| 6,055,457 A | 4/2000 | Bonner |
| 6,083,216 A | 7/2000 | Fischer, Sr. |
| 6,129,750 A | 10/2000 | Tockman et al. |
| 6,161,029 A | 12/2000 | Spreigl et al. |
| 6,181,971 B1 | 1/2001 | Doan |
| 6,256,541 B1 | 7/2001 | Heil et al. |
| 6,256,542 B1 | 7/2001 | Marshall et al. |
| 6,273,879 B1 | 8/2001 | Keith et al. |
| 6,289,251 B1 | 9/2001 | Huepenbecker et al. |
| 6,301,507 B1 | 10/2001 | Bakels et al. |
| 6,321,123 B1 | 11/2001 | Morris et al. |
| 6,324,415 B1 | 11/2001 | Spehr et al. |
| 6,363,288 B1 | 3/2002 | Bush et al. |
| 6,366,820 B1 | 4/2002 | Doan et al. |
| 6,374,476 B1 | 4/2002 | Ponzi et al. |
| 6,430,449 B1 | 8/2002 | Hsu et al. |
| 6,434,430 B2 | 8/2002 | Borgersen et al. |
| 6,456,888 B1 | 9/2002 | Skinner et al. |
| 6,456,890 B2 | 9/2002 | Pianca et al. |
| 6,477,427 B1 | 11/2002 | Stolz et al. |
| 6,500,174 B1 | 12/2002 | Maguire et al. |
| 6,501,990 B1 | 12/2002 | Sundberg et al. |
| 6,501,991 B1 | 12/2002 | Honeck et al. |
| 6,516,232 B2 | 2/2003 | Skinner |
| 6,567,704 B2 | 5/2003 | Sundquist et al. |
| 6,580,949 B1 | 6/2003 | Tsuboi et al. |
| 6,584,362 B1 | 6/2003 | Scheiner et al. |
| 6,611,720 B2 | 8/2003 | Hata et al. |
| 6,650,945 B2 | 11/2003 | Helland et al. |
| 6,669,691 B1 | 12/2003 | Taimisto |
| 6,697,675 B1 | 2/2004 | Safarevich et al. |
| 6,721,598 B1 | 4/2004 | Helland et al. |
| 6,748,277 B1 | 6/2004 | Chitre et al. |
| 6,757,970 B1 | 7/2004 | Kuzma et al. |
| 6,801,809 B2 | 10/2004 | Laske et al. |
| 6,843,870 B1 | 1/2005 | Bluger |
| 6,879,861 B2 | 4/2005 | Benz et al. |
| 6,882,886 B1 | 4/2005 | Witte et al. |
| 6,895,277 B2 | 5/2005 | Westlund et al. |
| 6,912,423 B2 | 6/2005 | Ley et al. |
| 6,915,169 B2 | 7/2005 | Flynn et al. |
| 6,968,236 B2 | 11/2005 | Hagele |
| 6,978,185 B2 | 12/2005 | Osypka |
| 6,983,185 B2 | 1/2006 | Ley et al. |
| 7,013,182 B1 | 3/2006 | Krishnan |
| 7,271,364 B1 | 9/2007 | Bye et al. |
| 7,917,229 B2 | 3/2011 | Zarembo et al. |
| 8,219,209 B2 | 7/2012 | Arnholt et al. |
| 8,364,282 B2 | 1/2013 | Zarembo et al. |
| 8,442,648 B2 | 5/2013 | Arnholt et al. |
| 2002/0082651 A1 | 6/2002 | Stahmann et al. |
| 2002/0107551 A1 | 8/2002 | Stahmann et al. |
| 2002/0143377 A1 | 10/2002 | Wessman et al. |
| 2003/0036779 A1 | 2/2003 | Westlund et al. |
| 2003/0040787 A1 | 2/2003 | Flynn et al. |
| 2003/0069625 A1 | 4/2003 | Ley et al. |
| 2003/0074031 A1 | 4/2003 | Ley et al. |
| 2003/0105505 A1 | 6/2003 | Pianca |
| 2003/0130610 A1 | 7/2003 | Mager et al. |
| 2003/0139794 A1 | 7/2003 | Jenney et al. |
| 2003/0153967 A1 | 8/2003 | Koblish et al. |
| 2003/0204229 A1 | 10/2003 | Stokes |
| 2003/0204230 A1 | 10/2003 | Yang et al. |
| 2004/0064172 A1* | 4/2004 | McVenes et al. ............. 607/122 |
| 2004/0064173 A1 | 4/2004 | Hine et al. |
| 2004/0064174 A1 | 4/2004 | Belden |
| 2004/0093052 A1 | 5/2004 | Westlund et al. |
| 2004/0143314 A1 | 7/2004 | Sommer et al. |
| 2004/0172116 A1 | 9/2004 | Seifert et al. |
| 2004/0260371 A1 | 12/2004 | Greenland et al. |
| 2004/0260374 A1 | 12/2004 | Zhang et al. |
| 2004/0260375 A1 | 12/2004 | Zhang et al. |
| 2005/0004642 A1 | 1/2005 | Shoberg |
| 2005/0010095 A1 | 1/2005 | Stewart et al. |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0027343 A1 | 2/2005 | Westlund et al. |
| 2005/0084672 A1 | 4/2005 | O'Brien |
| 2005/0095892 A1 | 5/2005 | Fukuyama |
| 2005/0202703 A1 | 9/2005 | Westlund et al. |
| 2005/0227398 A1 | 10/2005 | Anderson et al. |
| 2005/0228469 A1 | 10/2005 | Zarembo et al. |
| 2005/0234522 A1 | 10/2005 | Ley et al. |
| 2005/0267557 A1 | 12/2005 | Flynn et al. |
| 2006/0015164 A1 | 1/2006 | Partridge et al. |
| 2006/0036307 A1 | 2/2006 | Zarembo et al. |
| 2006/0089698 A1 | 4/2006 | Sundberg et al. |
| 2006/0100711 A1 | 5/2006 | Cauthen |
| 2006/0129220 A1 | 6/2006 | Koop et al. |
| 2006/0241734 A1 | 10/2006 | Marshall et al. |
| 2006/0259106 A1 | 11/2006 | Arnholt et al. |
| 2007/0055334 A1 | 3/2007 | Haldeman et al. |
| 2007/0066998 A1 | 3/2007 | Hansen et al. |
| 2007/0168004 A1 | 7/2007 | Walter |
| 2007/0250144 A1 | 10/2007 | Falk et al. |
| 2007/0255256 A1 | 11/2007 | Fischer, Jr. et al. |
| 2007/0255378 A1 | 11/2007 | Polkinghorne et al. |
| 2008/0046059 A1 | 2/2008 | Zarembo et al. |
| 2008/0057784 A1 | 3/2008 | Zarembo et al. |
| 2010/0042190 A1 | 2/2010 | Arnholt et al. |
| 2011/0112616 A1 | 5/2011 | Zarembo et al. |
| 2012/0253444 A1 | 10/2012 | Arnholt et al. |
| 2013/0116766 A1 | 5/2013 | Zarembo et al. |

\* cited by examiner

IMPLANTABLE MEDICAL LEAD HAVING REDUCED DIMENSION TUBING TRANSITION

CROSS-REFERENCE TO RELATED APPLICATION

This application is a continuation of U.S. application Ser. No. 13/526,071, filed Jun. 18, 2012, which itself is a continuation of U.S. application Ser. No. 12/534,114, filed Aug. 1, 2009, now U.S. Pat. No. 8,219,209, which claims the benefit of U.S. Provisional Application No. 61/089,330, filed Aug. 15, 2008, which are herein incorporated by reference in their entirety.

BACKGROUND

Medical leads typically have an elongate lead body that is used to deliver a therapy (e.g., one or more electrical pulses) to a location of interest within a patient. Many leads have one or more electrodes (e.g., ring electrodes or coil electrodes) disposed along the lead body. Some such leads also have a fixation member (e.g., an active fixation member) at the distal end of the lead body for fixing the lead body at a desired location within a patient's body. There is a need in the art for alternative designs and methods of construction for leads.

SUMMARY

In one embodiment of the invention, a medical lead comprises a multilumen tube having a distal end and a proximal end and a wall. The wall defines at least three lumens along a first longitudinal portion of the tube and less than three lumens along a second longitudinal portion of the tube. A first, continuous lumen extends through both the first and second portions and the wall is substantially continuous through both the first and second longitudinal portions. A proximal connector is disposed at the proximal end of the medical lead and the proximal connector is adapted to connect the lead to an implantable medical device. A fixation member is disposed on a distal end of the lead body and the fixation member has a fixation helix that is adapted to fix the lead at a site within a patient. A conductor member is disposed in the continuous lumen and electrically couples the proximal connector to the fixation member. The medical lead also has a distal tip portion, and the fixation member at least partially disposed within the distal tip portion. The second portion of the multilumen tube is connected with the distal tip portion, providing a fluid-tight passageway extending through the first and second portions of the multilumen tube and into the distal tip portion.

In another embodiment of the present invention, a medical lead comprises a multilumen tube defining a first number of lumens along a first longitudinal portion of the tube and a second number of lumens along a second longitudinal portion of the tube. The first number of lumens is larger than the second number of lumens. A continuous lumen extends through both the first and second portions and the wall is substantially continuous through both the first and second longitudinal portions. A fixation member is disposed on a distal end of the lead body, and the fixation member has a fixation helix that is adapted to fix the lead at a site within a patient. The medical lead also has a distal tip portion, and the fixation member at least partially disposed within the distal tip portion. A fluid tight seal is formed between the second portion of the multilumen tube and the distal tip portion, providing a fluid-tight passageway through the first and second portions of the multilumen tube, into the distal tip portion and to the fixation member.

In yet another embodiment of the present invention, a method of manufacturing a medical lead comprises providing a multilumen tube having a distal end and a proximal end and a first longitudinal axis, the tube defining a lumen that defines a second longitudinal axis that is non-coaxial with the first longitudinal axis. The method further comprises removing a first portion of a cross-section of the tube along a desired portion of the length of the tube while maintaining the lumen. The multilumen tube is rotated about the second longitudinal axis and a second portion of a cross-section of the tube is removed along the desired portion of the length of the tube. The multilumen tube is incorporating the tube into a lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
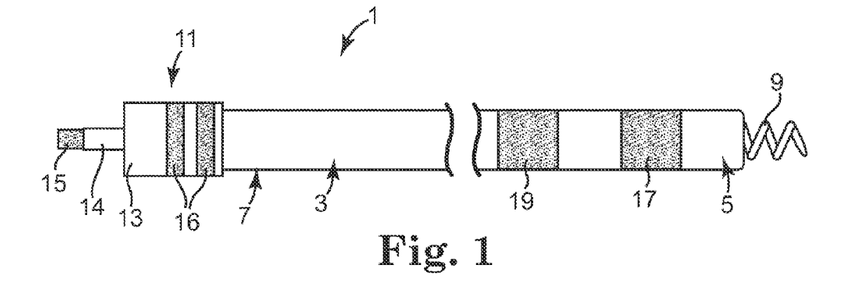
FIG. 1 is a plan view of a medical lead according to embodiments of the present invention.

FIG. 1 shows a medical lead 1 according to embodiments of the present invention. The medical lead 1 has a lead body 3 with a distal portion 5 and a proximal portion 7. A fixation helix 9 is disposed on the lead body distal portion 5. The fixation helix 9 is configured to anchor the lead body 3 at a desired location within a patient, as further discussed below.

Figure 5:
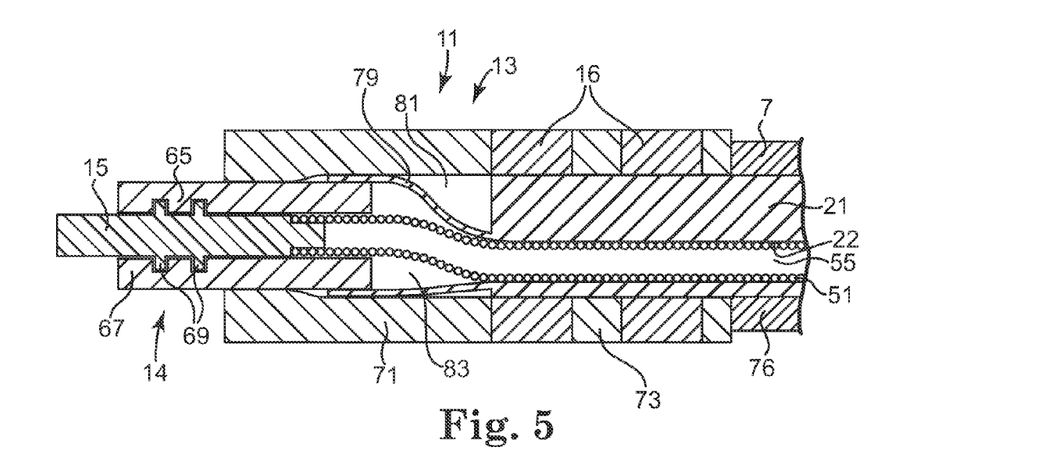
FIG. 5 is a longitudinal cross-sectional view of a proximal portion of a lead according to some embodiments of the present invention.

In addition, the lead 1 has a proximal connector 11 disposed on the lead body proximal portion 7. The proximal connector 11 is configured to couple to a cardiac rhythm management device (not shown). The proximal connector 11 has a connector body 13 and a terminal pin 14 extending proximally from the connector body 13. In some embodiments, and as shown in FIGS. 1 and 5, the connector body 13 has a larger outer dimension than the terminal pin 14.

As shown in FIG. 1, the terminal pin 14 includes a single electrical contact 15. In other embodiments, the terminal pin 14 has more than one, or two or more, electrical contacts formed thereon. Further, as shown in FIG. 1, the proximal connector body 13 has two ring contacts 16 disposed thereon. In other embodiments, the proximal connector body 13 has a single, one or more, two or more, or three or more ring contacts 16 disposed thereon.

Further, the lead 1 has one or more electrodes disposed thereon, for example two electrodes 17, 19 as shown in FIG. 1. In other embodiments, the lead 1 has more than two, three or more, or four or more electrodes, or any other suitable number of electrodes. In some exemplary embodiments, one or more of the electrodes 17, 19 are shock coils that are disposed along the lead body 3. In other exemplary embodiments, the one or more electrodes 17, 19 are ring electrodes or tip electrodes. In some embodiments, each of the electrodes 17, 19 are electrically connected to at least one of the one or more ring contacts 16 on the proximal connector body 13, as further discussed below.

In some embodiments, the fixation helix 9 is rotatably fixed with respect to the lead body 3. In some such embodiments, the lead body 3 is torquable, allowing the fixation helix 9 to be implanted in body tissue by bringing the fixation helix 9 into contact with body tissue and torquing the lead body 3 to provide torque to the fixation helix 9. As the fixation helix 9 is turned, the fixation helix 9 essentially screws into body tissue at the target location.

Figure 2:
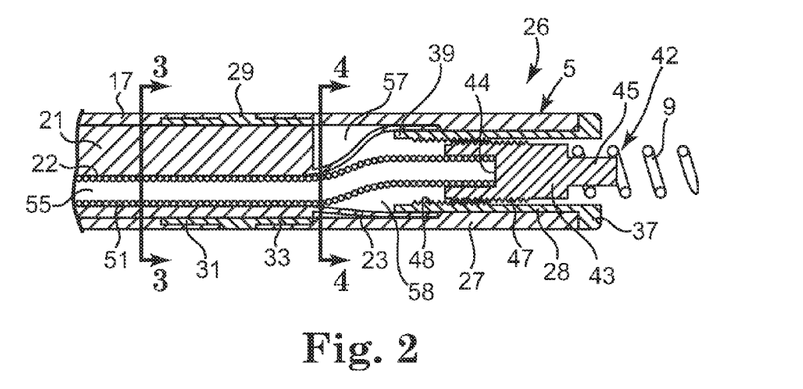
FIG. 2 is a longitudinal cross-sectional view of a distal portion of a medical lead according to embodiments of the present invention.

In other embodiments, and as best shown in FIG. 2 (described below), the fixation helix 9 is rotatable with respect to the lead body 3. Further, as best shown in FIG. 5 (also described below), in some embodiments the terminal pin 14 is rotatable with respect to the proximal connector body 13 and the lead body 3. As described in detail below, in some embodiments the terminal pin 14 is connected to the fixation helix 9 such that providing torque to the rotatable portion of the terminal pin 14 imparts a torque on the fixation helix 9, facilitating the implantation of the fixation helix 9 at a desired location. Further, in some embodiments the fixation helix 9 is also provided with a mechanism that facilitates the extension and retraction of the fixation helix 9 from the lead body distal portion 5.

In some embodiments, the lead 1 is adapted to supply an electrical shock to a patient's heart via one or both of the electrodes 17, 19. In some such embodiments, the electrodes 17, 19 include a coil. In addition, in some embodiments the lead 1 is also adapted to provide a cardiac pacing signal and/or sense the electrical signals of a heart. For example, one or more of the fixation helix 9, a portion of the electrodes 17, 19, or optional additional electrodes such as ring electrodes (not shown) are configured to act as the poles of a pacing or sensing circuit. In some unipolar embodiments, one or more of the fixation helix 9, a portion of the electrodes 17, 19, and/or optional additional electrodes are adapted to act as one pole of the pace/sense circuit and the other pole of the pace/sense circuit is provided at a remote location within the patient's body or on the surface of the patient's body. In some bipolar embodiments, one or more of the fixation helix 9, a portion of the electrodes 17, 19, and/or optional additional electrodes are adapted to act as one pole of the pace/sense circuit and another of the fixation helix 9, a portion of the electrodes 17, 19 and/or optional additional electrodes are adapted to act as the other pole of the pace/sense circuit. For example, in some embodiments the fixation helix 9 is adapted to act as one pole of a bipolar pace/sense circuit and a portion of one or both of the electrodes 17, 19 and/or one or more optional additional ring electrodes are adapted to act as the other pole of the bipolar pace/sense circuit.

Figure 3:
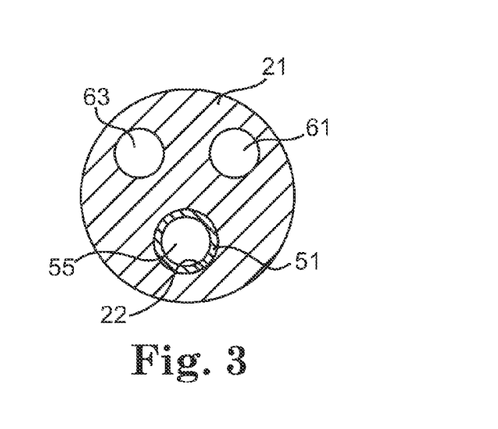
FIG. 3 is a cross-sectional view of a portion of the distal portion of FIG. 2 according to some embodiments of the present invention.

FIG. 2 shows a longitudinal cross-section of a distal portion of the lead 1 according to some embodiments of the present invention. FIGS. 3 and 4A-4C show cross-sections of the lead body 3 at certain longitudinal positions along the lead 1. As mentioned above, the lead 1 has a fixation helix 9 disposed on a lead body distal portion 5. The lead body 3 includes an elongate tubular member 21 that defines multiple lumens (as best shown in FIG. 3). In some embodiments, the multilumen tube 21 forms a central or inner portion of the lead body 3 and extends from a proximal portion to a distal portion of the lead body 3.

As shown in FIG. 2, the multilumen tube 21 has a tubular wall which defines a first lumen 22. The multilumen tube 21 has a first portion in which a first number of lumens are defined (shown best in FIG. 3) and a second, reduced dimension portion 23 in which a second number of lumens is defined (shown best in FIGS. 4A-4C). As shown in FIGS. 3 and 4A-4C, the first number of lumens is greater than the second number of lumens. In some embodiments, the multilumen tube 21 forms a continuous (i.e., monolithic) wall that extends along both the first portion and the second, reduced dimension portion 23. For example, the reduced dimension portion 23 is formed starting with a continuous (i.e., monolithic) multilumen tube and cutting away a portion of the multilumen tube 21, as further discussed below. As shown in FIGS. 3 and 4A-4C, in some embodiments the number of lumens in the first portion of the multilumen tube 21 is three lumens and the number of lumens in the reduced dimension portion 23 is one. However, the number of lumens in these two portions can vary depending on the application.

In some embodiments, the first lumen 22 extends through the multilumen tube 21 from a proximal end to a distal end of the multilumen tube 21. As shown in FIG. 2, in some embodiments the first lumen 22 extends through both the first portion of the multilumen tube 21 and the reduced dimension portion 23 of the multilumen tube 21. In some embodiments, the reduced dimension portion 23 has a reduced outer dimension relative to the portion of the multilumen tube 21 immediately proximal to the reduced dimension portion 23. As shown in FIG. 2, in some embodiments the reduction in outer diameter that forms the reduced dimension portion 23 is an abrupt change in outer dimension of the multilumen tube 21. In other embodiments, this change in outer dimension is gradual or it is reduced in a stepped manner.

In addition, in some embodiments the multilumen tube 21 comprises a flexible and/or stretchable material, for example silicone or polyurethane or any other suitable material. As further discussed below, in some embodiments stretchable material allows the reduced dimension portion 23 to be stretched in order to place the reduced dimension portion 23 over another portion of the lead 1.

The lead body distal portion 5 also includes a distal tip portion 26 that includes a distal outer member 27 and an insert 28. In some embodiments, the distal outer member 27 is attached to the multilumen tube 21. As shown in FIG. 2, the distal outer member 27 attaches to a connector member 29. The connector member 29 is in turn connected to the multilumen tube 21, and in some embodiments also connects to a distal end of the electrode 17. For example, the connector member 29 has a proximal flange portion 31 and a distal flange portion 33. The electrode distal end extends over and is attached to the proximal flange portion 31. A proximal portion of the distal outer member 27 extends over and is attached to the distal flange portion 33. In other embodiments, the distal outer member 27 and/or the electrode 17 attaches directly to the multilumen tube 21, or it attaches to another portion of the lead body 3.

Further, the insert 28 is sized and configured to fit within, and is affixed to, the distal outer member 27. In some embodiments, a distal end 37 of the insert 28 is shaped and configured to fit around the distal end of the distal outer member 27, forming a distal leading edge of the lead body 3. As shown in FIG. 2, the distal end 37 has rounded edges, providing for a generally atraumatic shape on the distal end of the lead body 3.

In addition, in some embodiments a distal portion of the distal outer member 27 has a reduced inner diameter relative to a proximal portion of the distal outer member 27. As shown in FIG. 2, a proximal portion 39 of the insert 28 extends proximal of this reduced inner diameter portion, forming a space between the inner surface of the distal outer member 27 and the outer surface of the insert proximal portion 39. In some embodiments, the space is an annular space, and the reduced dimension portion 23 is radially expanded or stretched and disposed around the insert proximal portion 39. In some embodiments, as shown in FIG. 2, the reduced dimension portion 23 forms a lap joint with the insert proximal portion 39. For example, a friction fit is formed therebetween and/or an adhesive is placed between the reduced dimension portion 23 and the insert 28.

In some embodiments, a fixation member 42 includes both the fixation helix 9 and a fixation helix base 43. The fixation helix base 43 is disposed within the insert 28, and the fixation helix base 43 has a fixation helix seating portion 45. In some embodiments, the seating portion 45 is a reduced dimension portion of the fixation helix base 43, facilitating the attachment of the fixation helix 9 to the fixation helix base 43 while still allowing the fixation member 42 as a whole to translate in and out of the insert 28.

As shown in FIG. 2, the fixation helix base 43 also has first threads 47 formed on an outer surface of the fixation helix base 43. In addition, second threads 48 are formed on an inner surface of the insert 28. The first and second threads 47, 48 are shaped and configured to mechanically engage one another such that rotating the fixation helix base 43 with respect to the lead body 3 (e.g., with respect to the insert 28), causes the fixation member 42 to move longitudinally with respect to the lead body 3 (e.g., with respect to the insert 28).

As shown in FIG. 2, the fixation helix base 43 defines a proximal opening 44. Further, extending through the first lumen 22 of the multilumen tube 21 is a conductor member 51. The conductor member 51 extends into, and is electrically coupled to, the fixation member 42 (e.g., electrically coupled within the proximal opening 44 of the fixation helix base 43, as shown).

In addition to electrically coupling to the fixation member, in some embodiments the conductor member 51 is also a torque transmission member, and the distal portion of the conductor member 51 is mechanically coupled to the fixation helix base 43. As discussed in more detail below, in some embodiments the conductor member 51 extends proximally to, and is mechanically coupled to, a rotatable portion of the terminal pin 14. The conductor member 51 transmits torque from a rotatable portion of the terminal pin 14 to the fixation member 42. As mentioned above, turning the fixation helix base 43 within the insert 28 causes the fixation member 42 as a whole to simultaneously rotate and move longitudinally, facilitating the implantation of the fixation helix 9. In some embodiments, the conductor member 51 is a coil member and the coil member is elongateable in order to accommodate the longitudinal movement of the fixation member 42.

As mentioned above, in some embodiments the fixation member 42 is electrically coupled to the conductor member 51. In some such embodiments, the fixation helix 9 is an active fixation helix. For example electric signals are transmitted between the fixation helix 9 and a portion of the terminal pin 14 via the conductor member 51. As such, the contact 15 on the terminal pin 14, the conductor member 51, the fixation helix base 43 and the fixation helix 9 are all electrically conductive such that a first electric pathway is formed between the contact 15 and the fixation helix 9.

In addition, as shown in FIGS. 2-4C, the conductor member 51 defines a lumen 55. In some such embodiments, a stylet (not shown) is provided, and the stylet is sized and configured to be disposed within the lumen 55. Further, in some embodiments the stylet is torqueable and facilitates the transfer of torque and/or axial force from the terminal pin to the fixation helix 9. In other embodiments, the stylet may impart a shape to the lead 1 and/or the stylet may impart increased stiffness to certain portions of the lead 1.

FIGS. 3 and 4A-4C show cross-sections of the multilumen tube 21 according to various embodiments of the present invention. It is noted that, although FIG. 2 indicates that FIGS. 3 and 4A-4C show cross-sections of the entire lead 1, for clarity FIGS. 3 and 4A-4C show only the multilumen tube 21 and the conductor member 51.

FIG. 3 shows a cross section of the multilumen tube 21 that has not been cut down or reduced in outer dimension. As shown, in some embodiments the multilumen tube 21 has three lumens 22, 61, 63. In other embodiments, the multilumen tube 21 has a single lumen, two or more lumens (e.g., lumen 22 with one lumen generally vertically aligned with lumen 22), three or more lumens, four or more lumens, or any other suitable number of lumens. Further, in some embodiments one or more of the lumens are offset from the longitudinal axis of the multilumen tube 21. For example, the first lumen 22 has a longitudinal axis that is non-coaxial with respect to the longitudinal axis of the multilumen tube 21. As further discussed below, in some embodiments the lumens 61, 63 provide a passageway through which conductors can pass and the conductors electrically connect one or more of electrodes 17, 19 to the one or more electrical contacts 16.

Figure 4A:
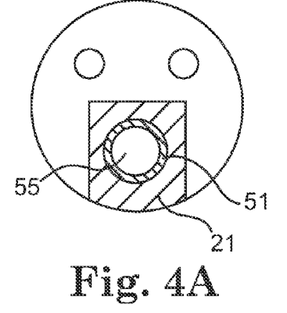
FIGS. 4A-4C are cross-sectional views of a portion of the distal portion of FIG. 2 according to various embodiments of the present invention.
Figure 4B:
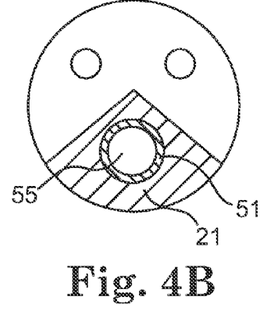
Figure 4C:
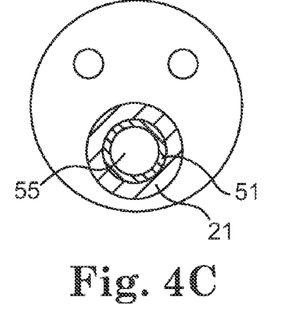

FIGS. 4A-4C show cross-sections of the reduced dimension portion 23 of the multilumen tube 21. The portions of the multilumen tube 21 that remain after portions of the tube have been cut away are shown using a cross-hatched pattern. FIG. 4A shows one embodiment of a reduced dimension portion that results from removing material from the multilumen tube 21 generally along three planes. The cuts are made in order to both reduce the outer dimension of the multilumen tube 21 and reduce the number of lumens along a reduced dimension portion 23 of the multilumen tube 21. FIG. 4B shows another embodiment of a reduced dimension portion that results from removing material from the multilumen tube 21 generally along two planes. The two flat portions of the reduced dimension portion 23 indicate where the two portions of material are removed, forming a reduced dimension portion of the multilumen tube 21 that has a reduced number of lumens. FIG. 4C shows yet another embodiment of a reduced dimension portion 23 that results from removing material from the multilumen tube 21 in order to form a round cross-sectional shape in the reduced dimension portion 23.

In addition, other cross-sectional shapes are possible for the reduced dimension portion 23 and for the other reduced dimension portions described herein. For example, in some embodiments, material is removed from the multilumen tube along a single plane. In some embodiments the reduced dimension portion 23 and the other reduced dimension portions described herein define more than one lumen. In other embodiments, the reduced dimension portion 23 has no lumen extending therethrough (e.g., the lumens terminate at the reduced dimension portion). In addition, although embodiments described above generally refer to a multilumen tube, other embodiments in which the tube has a single lumen are also contemplated. In some such embodiments, the single lumen continues through the reduced dimension portion (the single lumen has a reduced thickness wall), while in other embodiments the reduced dimension portion does not contain the lumen (e.g., the lumen terminates at the reduced dimension portion and the reduced dimension portion has a solid cross-section).

As shown in FIG. 2, the reduced dimension portion 23 is stretched or expanded in order to be disposed around a portion of the distal tip portion 26 (e.g., the insert 28). As such, the lumen 22 formed by the multilumen tube 21 is continuous, and extends from a proximal portion of the multilumen tube 21, through the reduced dimension portion 23 of the multilumen tube 21 and connects to the insert 28. In addition, in some embodiments the joint between the reduced dimension portion 23 and the distal tip portion 26 forms a fluid tight seal in order to prevent fluids from entering the lumen 22. In some embodiments, this fluid tight lumen 22 prevents interference with the electrical signals that are being passed along the conductor member 51. As such, a fluid-tight pathway extends through the lumen 22 from the proximal portion of the multilumen tube 21, through the reduced dimension portion 23 and further through the distal tip portion 26 to the fixation member 42. An O-ring or some other type of seal (not shown) may also be placed between the fixation member 42 (e.g., the fixation helix base 43) and the insert 28 in order to prevent fluids from entering the fluid-tight pathway through the distal end of the lead 1.

In addition, as shown in FIG. 2, a space 57 is formed within the lead 1 around the reduced dimension portion 23. In some embodiments, this space 57 is kept open, while in other embodiments the space 57 is partially or entirely filled, for example with a medical adhesive or other suitable filler material. In addition, in some embodiments a space 58 is formed within the reduced dimension portion 23. In some embodiments, this space 58 is kept open in order to allow for the rotation of the conductor member 51. In other embodiments, the space 58 is partially or entirely filled, for example with a medical adhesive or other suitable filler.

In the embodiment shown in FIG. 2, the reduced dimension portion 23 is stretched or expanded in order to be disposed around a portion of the distal tip portion 26 (e.g., the proximal end 39 of the insert 28). As shown, a space is formed between the insert proximal end 39 and the inner surface of the distal outer member 27. In other embodiments, the insert proximal end 39 has a portion with a reduced outer dimension in order to facilitate the placement of the reduced dimension portion 23 of the multilumen tube 21 over the insert 28. For example, the insert proximal end 39 may have a portion that is tapered or stepped down to a smaller outer dimension so that the reduced dimension portion 23 is required to be stretched or expanded a lesser amount relative to the embodiment shown in FIG. 2. As another example, a separate extension member (not shown) may extend proximally from the distal tip portion 26 (e.g., from the insert proximal portion 39) and the separate extension may be tapered or stepped down to a smaller outer dimension.

FIG. 5 shows a longitudinal cross-section of the proximal connector 11 of the lead 1 according to some embodiments of the present invention. As mentioned above, the proximal connector 11 has a connector body 13 and a terminal pin 14 extending proximally from the connector body 13. A portion of the outer surface of the terminal pin 14 defines a first electrical contact 15.

As shown in FIG. 5, the terminal pin 14 has an outer body portion 65 surrounding an inner body portion 67. A portion of the inner body portion 67 extends proximally from the outer body portion 65, forming the first electrical contact 15. In addition, in some embodiments the inner body portion 67 has an outer shape that mechanically interacts with an inner shape of the outer body portion 65, maintaining the inner body portion 67 in a longitudinally fixed position while allowing rotation of the inner body portion 67 with respect to the outer body portion 65. For example, the inner body portion 67 has one or more, or two or more annular shaped protrusions 69 formed thereon. Further, the outer body portion 65 has annular grooves that correspond to the one or more annular protrusions 69. The grooves and protrusions mechanically interact to allow the inner body portion 67 to rotate within the outer body portion 65.

The connector body 13 has a proximal portion 71. In some embodiments, the connector body proximal portion 71 surrounds, and is affixed to, the outer body portion 65 of the terminal pin 14. In addition, one or more electrical contacts 16 are disposed on the connector body 13, for example embedded in the connector body 13. As shown in FIG. 5, the connector body 13 also has an insulative portion 73 that is disposed between the electrical contacts 16 in order to electrically isolate the electrical contacts 16 from one another.

In addition, as shown in FIG. 5, in some embodiments a distal portion of the connector body 13 surrounds, and is affixed to, other portions of the lead body proximal portion 7, for example the multilumen tube 21 and/or a lead outer layer 76. The multilumen tube 21 has a reduced dimension portion 79, which in some embodiments is similar to any of the reduced dimension portions 23 described above. Similar to the reduced dimension portion 23, the reduced dimension portion 79 is formed by a continuous (i.e., monolithic) portion of the wall of the multilumen tube 21. The wall is continuous (i.e., monolithic) from adjacent to the reduced dimension portion 79 and through the reduced dimension portion 79 and in some embodiments the continuous wall extends the entire, or substantially the entire length of the multilumen tube 21.

Similar to the reduced dimension portion 23, the reduced dimension portion 79 can also be stretched in order to be placed over a portion of the proximal connector 11. For example, as shown in FIG. 5, a proximal end of the reduced dimension portion 79 is stretched to create a larger inner opening. The larger inner opening is sufficiently large to fit over a distal portion of the outer body portion 65 of the terminal pin 14, for example forming a lap joint between the outer body portion 65 and the reduced dimension portion 79. The joint between the outer body portion 65 and the reduced dimension portion 79 can be formed by friction fit or with the use of adhesive, or with any other suitable technique. In some embodiments, the joint between the outer body portion 65 and the reduced dimension portion 79 facilitates the formation of a fluid tight lumen from the outer body portion 65, through the first lumen 22 of the multilumen tube 21, to the tip of the lead, as described above with respect to FIG. 2. Also, as mentioned above with respect to spaces 57, 58, the space 81 and/or the space 83 may be left open on either or both of the spaces 81, 83 may be filled with a medical adhesive or another suitable material.

Further, as discussed above, the multilumen tube 21 defines a first lumen 22 through which the conductor member 51 extends and in some embodiments the conductor member 51 is rotatable with respect to the multilumen tube 21. The conductor member 51 extends proximally to the inner body portion 67 and is affixed to the inner body portion 67, which, as mentioned above, is rotatable with respect to the outer body portion 65 (and, as such, is rotatable with respect to the proximal connector 11 and the lead body proximal portion 7). As such, torque can be transmitted from the inner body portion 67 of the terminal pin 14 to the fixation helix 9 via the conductor member 51.

Figure 6:
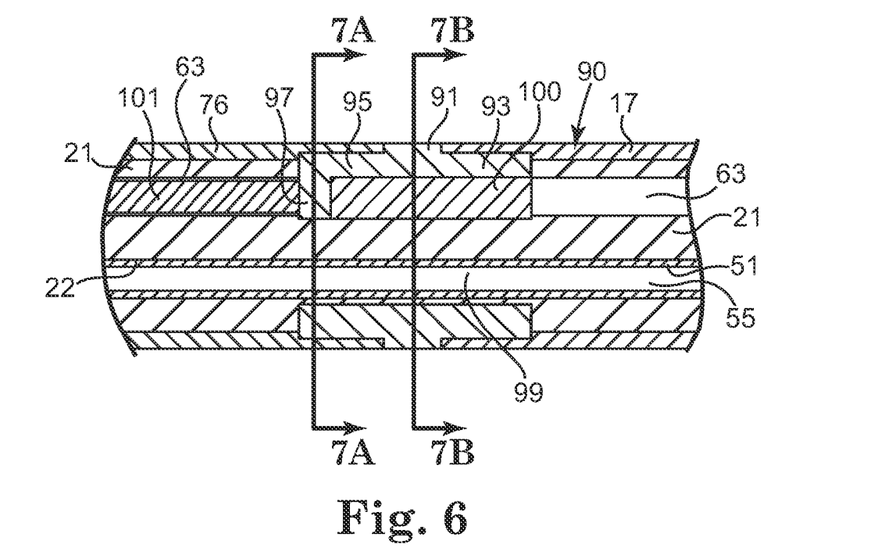
FIG. 6 is a longitudinal cross-sectional view of a portion of an electrode according to some embodiments of the present invention.

FIG. 6 shows a longitudinal cross-section of the lead body near a proximal end of an electrode 17 according to some embodiments of the present invention. The electrode 17 includes a coil 90 and a fitting 91. The fitting 91 is disposed along the lead 1, and the fitting 91 has a distal flange portion 93 and a proximal flange portion 95. The proximal end of the coil 90 extends over the distal flange portion 93 and is affixed to the distal flange portion 93 by any of a variety of methods known in the art, including by mechanical fit, by adhesive, by welding, brazing, soldering, crimping, or staking, or by any other suitable method. In some embodiments, affixing the coil electrode 17 to the fitting 91 forms an electrical connection therebetween. In some embodiments, a portion of lead 1 (e.g., the outer layer 76) extends over the proximal flange portion 95. The portion of the lead 1 extending over the proximal flange portion 95 is affixed to the proximal flange portion 95, for example by shrink fitting, by extrusion, by dip coating, by adhesive, or by any other suitable method.

Figure 7A:
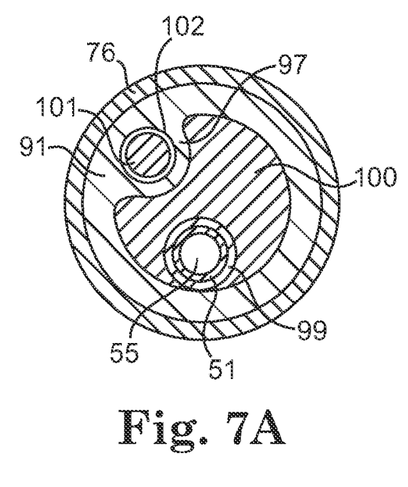
FIGS. 7A and 7B are cross-sectional views of a portion of the electrode of FIG. 6 according to some embodiments of the present invention.

The fitting 91 also has an eyelet 97, which provides a point of connection for a conductor member, as best shown in FIG. 7A and as further discussed below. The multilumen tube 21 extends through the fitting 91. For example, the multilumen tube 21 has a reduced dimension portion 99, which can be similar in cross-sectional shape to any of the reduced dimension portions described above. Further, as mentioned above with respect to reduced dimension portions 23 and 79, reduced dimension portion 99 is defined by a wall of the multilumen tube 21, the wall being a continuous (i.e., monolithic) wall from adjacent the reduced dimension portion 99 and through the reduced dimension portion 99. In some embodiments, the multilumen tube 21 is reduced in dimension only through the fitting 91 (as shown in FIG. 6), and in other embodiments the multilumen tube 21 is reduced in dimension through the fitting 91 and distal of the fitting 91. The reduced dimension portion 99 is sized to fit through the open area 100 of the fitting 91, as shown best in FIGS. 7A and 7B. In some embodiments the open area 100 within the fitting 91 that is not occupied by the reduced dimension portion 99 remains open, while in other embodiments the open area 100 is entirely or partially filled with a medical adhesive or with another suitable filler material.

As described above, the multilumen tube 21 defines the first lumen 22 along with the second lumen 63. Extending through the first lumen 22 is the conductor member 51, while a second conductor member 101 extends through the second lumen 63.

Figure 7B:
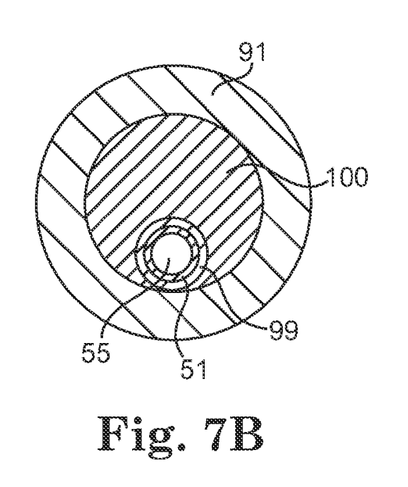

Shown in FIGS. 7A and 7B are cross-sections of FIG. 6. FIG. 7A shows the eyelet 97 defining an opening 102. The eyelet 97 is slightly offset from the longitudinal axis of the fitting 91, which in some embodiments ensures that the eyelet 97 is aligned with the second lumen 63. As such, the second conductor member 101 can extend into the opening 102. In some embodiments, the second conductor member 101 is affixed to the eyelet 97, for example by welding, soldering, crimping or staking, or by any other suitable method. In some embodiments, affixing the second conductor member 101 to the eyelet 97 forms an electrical connection. As such, an electrical pathway is formed from the second conductor member 101, to the fitting 91, and to the electrode 17. In addition to the fittings described herein, a variety of other types of fittings may be used to facilitate the connection of a conductor member to a ring electrode or coil electrode. For example, U.S. Patent Application No. 61/074,304, titled "Methods and Devices for Joining Cables," filed Jun. 20, 2008 describes some such fittings, and is incorporated by reference herein in its entirety.

As shown in FIG. 7B, the reduced dimension portion 99 extends through the fitting 91, and is surrounded by the space 100, which, as mentioned above, in some embodiments is partially or entirely filled by a filling material. In addition, the reduced dimension portion 99 can be circular in cross-section (as shown in FIGS. 6-7B), or it can be one of the shapes shown in FIGS. 4A and 4B, or any other suitable shape.

Further, in embodiments where more than one electrode is disposed along the lead 1, more than one lumen is maintained through the fitting in order to provide a passageway for a conductor member to reach the distal electrode(s). As such, the reduced dimension portion 99 has any desired cross-sectional shape, and may define zero, one or more, two or more, or three or more, lumens.

Further, in some embodiments the conductors that extend from the electrodes 17, 19 to the ring contacts 16 (e.g., the second conductor member 101) are attached to the ring contacts 16 in a manner similar to that described with respect to FIGS. 6-7B. For example, in some embodiments, the ring contacts 16 are formed from an outer surface of a ring-like structure such as the fitting 91 described above. In this manner, an electrical pathway is formed between one or more of the ring contacts 16 and one of the electrodes 17, 19.

The embodiments above have been described with respect to leads that comprise shocking electrodes. In some embodiments, in addition to, or in place of, the shocking electrodes, the lead 1 has ring electrodes, and the ring electrodes are disposed along the lead body similar to the fitting 91 shown in FIG. 6. The ring electrodes may be adapted for pacing and/or sensing electrical signals of the heart, for example for use as a pacing lead. In some such embodiments, electrical conductors are attached to the ring electrodes in a manner similar to that shown in FIGS. 6-7A. Further, although the fixation helixes discussed above are described as active helixes, they may also be passive (i.e., non-electrically active). Other fixation mechanisms known in the art may also be used in place of the fixation helix.

In another embodiment of the present invention, a method of manufacturing a lead includes providing a multilumen tube (e.g., any of the multilumen tubes described above) and removing a portion of a multilumen tube to form a reduced dimension portion, for example any of the reduced dimension portions mentioned above.

In a method of the present invention, a multilumen tube is provided, for example any of the multilumen tubes described above in which the one or more of the lumens is eccentrically disposed in the multilumen tube. For example, the first lumen 22, as shown best in FIGS. 2 and 3, has a longitudinal axis that is offset from the longitudinal axis of the multilumen tube 21. As such, in order to remove material from the multilumen tube 21 and create a reduced dimension portion that maintains lumen 22 and is substantially aligned with the longitudinal axis of the lumen 22, the multilumen tube 21 is rotated about the longitudinal axis of the lumen 22 when removing material from the multilumen tube 21. For example, a portion of the cross-section of the multilumen tube 21 is removed along a desired length of the multilumen tube 21, the multilumen tube 21 is rotated about the longitudinal axis of the lumen 22, and another portion of the cross-section of the multilumen tube 21 is removed. This process can be repeated any number of times, for example making two or more, three or more, or four or more cuts or ablations. If a large number of cuts or ablations are made and the multilumen tube 21 is rotated a relatively small amount between cuts or ablations, a cross-section of the reduced dimension portion may have a substantially round outer shape, as shown in FIG. 4C.

Figure 8:
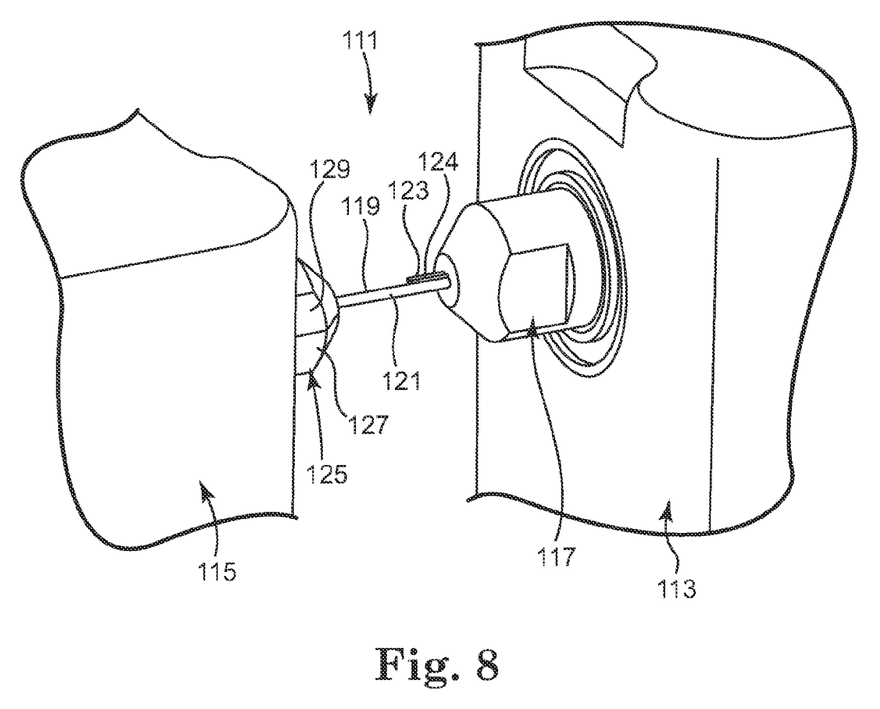
FIG. 8 is a perspective view of a fixture according to some embodiments of the present invention.

FIG. 8 shows a fixture 111 for removing a portion of a multilumen tube. The fixture 111 has a support with a first side 113 and a second side 115. The first side 113 has a first head 117 and the second side 115 has a second head 125. The first head 117 has jig 119 affixed thereto, and the jig 119 has one or more, two or more, three or more, or four or more longitudinal jig members. For example, as shown in FIG. 8, the jig 119 has a first longitudinal jig member 121, a second longitudinal jig member 123 and a third longitudinal jig member 124. In some embodiments, the longitudinal jig members 121, 123, 124 are rods, while in other embodiments the longitudinal jig members 121, 123, 124 are tubular members, or they are any other suitable longitudinal member. In some embodiments, each of the longitudinal jig members 121, 123, 124 are affixed to the first head 117 and extend across toward the second head 125. As shown in FIG. 8, the first longitudinal jig member 121 is longer than the other longitudinal jig members 123, 124, and in some such embodiments the second and third longitudinal jig members 123, 124 are the same length. Further, in some embodiments, the first longitudinal jig member 121 has a greater outer dimension than the second and third longitudinal jig members 123, 124.

In some embodiments, the number, size and configuration of the longitudinal jig members are adapted to match with the number, size and configuration of the lumens of the multilumen tube. For example, the first longitudinal jig member 121 is sized and configured to fit within the first lumen 22 of the multilumen tube 21, the second longitudinal jig member 123 is sized and configured to fit within the second lumen 63, and the third longitudinal jig member 124 is sized and configured to fit within the third lumen 61.

The second head 125 has a bottom portion 127 and a top portion 129. In some embodiments, the top and bottom portions are openable with respect to one another, for example as disclosed in U.S. Pat. No. 7,271,364, filed Sep. 18, 2007, entitled "Laser Welding Fixture and Method," which is herein incorporated by reference in its entirety. In some embodiments, one or more of the longitudinal jig members 121, 123, 124 extend to, or extend close to, the second head 125. In some other embodiments, the longitudinal jig members 121, 123, 124 extend to, and into, the second head 125. In some embodiments, the first and second heads 117, 125 are driven (e.g., by a motor) and they are coordinated such that they are rotated simultaneously at the same rate within the fixture 111.

A multilumen tube is fed over the jig 119 so that the longitudinal jig members 121, 123, 124 extend into the lumens of the multilumen tube. For example, the multilumen tube 21 is disposed over the jig 119 so that the first lumen 22 is disposed on jig member 121, the second lumen 63 is disposed on jig member 123 and the third lumen 61 is disposed on jig member 124. The jig member 121 is centered on the heads 117, 125. The multilumen tube extends through a channel (not show) in the second head 125 and, in some embodiments, through all or a portion of the second side 115.

In order to remove material from the multilumen tube, any suitable cutting or ablating apparatus may be used. For example, in some embodiments the cutting or ablation apparatus (not shown) is a physical ablation tool (e.g., a grinder) or a laser. In some embodiments, the cutting or ablation apparatus is positioned in order to ablate or cut material away from the multilumen tube along the longitudinal jig member 121 that is centered on the heads 117, 125. In some embodiments, the cutting or ablation apparatus moves within the fixture 111 in order to facilitate cutting or ablating along a desired length of the multilumen tube. In some embodiments, the cutting or ablating apparatus cuts or ablates along the multilumen tube, forming a generally flat surface along the multilumen tube (as shown in FIGS. 4A and 4B). The fixture 111 can be used to rotate the multilumen tube about the longitudinal axis of the lumen in which the first jig 121 is disposed, and a second cut or ablation is performed. This can be repeated a number of times and at the necessary angles to form the desired shape. In some embodiments, the multilumen tube is cut or ablated numerous times and the multilumen tube is rotated a small amount between cuts or ablations in order to form a reduced dimension portion with an outer surface that defines a substantially round cross-section (see, for example, FIG. 4C). Further, in some embodiments the multilumen tube with one or more reduced dimension portions is then incorporated into a lead as shown in FIGS. 1-7B and as described above.

In some embodiments in which the reduced dimension portion is formed along an intermediate portion of the multilumen tube (e.g., as shown in FIG. 6), the multilumen tube (including the reduced dimension portion) is stretched in order to neck down the entire multilumen tube. The reduced dimension of the entire multilumen tube allows a fitting or a ring electrode to be passed over the multilumen tube and disposed in the reduced dimension portion, as shown in FIG. 6. In some embodiments, a ring electrode or a fitting is a continuous, unbroken ring of material that is placed in the reduced dimension portion in this manner.

In some embodiments, some of the leads described above can have the capability both to shock the heart and pace and/or sense the rhythm of the heart. For example, in some embodiments the lead 1 shown in FIG. 1 has multiple shock coils 17, 19 disposed thereon along with a fixation helix 9. The fixation helix 9 is electrically coupled to the terminal pin electrical contact 15, whereas the shock coils 17, 19 are each electrically coupled to one of the ring contacts 16. In some such embodiments, the lead 1 is adapted to shock a heart using one or both of the shock coils 17, 19. In addition, a portion of one or both of the shock coils 17, 19 (e.g., a fitting at one end or both ends of one or both of the shock coils 17, 19) is adapted to be one pole of a pace/sense circuit. In some embodiments, the other pole of the pace/sense circuit is the fixation helix 9. In other embodiments, a portion of one or both of the shock coils 17, 19 and/or the fixation helix 9 are configured to operate as one pole of the pace/sense circuit and the other pole of the pace/sense circuit is disposed at another location within the patient's body or on an outer surface of the patient's body.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical lead comprising:
    a multilumen tube having a distal end and a proximal end and a wall, the wall defining at least three lumens along a first longitudinal portion of the tube and less than three lumens along a second longitudinal portion of the tube, wherein a first, continuous lumen extends through both the first and second portions, wherein the wall is substantially continuous through both the first and second longitudinal portions;

a proximal connector disposed at the proximal end of the medical lead, the proximal connector adapted to connect the lead to an implantable medical device; and a distal tip portion;

wherein the second portion of the multilumen tube is connected with the distal tip portion, providing a fluid-tight passageway extending through the first and second portions of the multilumen tube and into the distal tip portion.

2. The medical lead of claim 1, wherein the distal tip portion has a distal outer member and a distal inner member disposed within the distal outer member, wherein a space is formed between an outer surface of a proximal portion of the distal inner member and the inner surface of the distal outer member, and wherein the second portion of the multilumen tube is disposed within the space and forms a fluid tight seal with the distal inner member.

3. The medical lead of claim 1, wherein the multilumen tube comprises a flexible material and wherein the second longitudinal portion of the multilumen tube is stretched to fit over a portion of the distal tip portion.

4. The medical lead of claim 3, wherein the material is silicone.

5. The medical lead of claim 1, wherein the second longitudinal portion of the multilumen tube defines a single lumen.

6. The medical lead of claim 1, wherein the wall of the multilumen tube is continuous from the distal end to the proximal end of the multilumen tube.

7. The medical lead of claim 1, wherein the multilumen tube is continuous through the first longitudinal portion of the tube and the second longitudinal portion of the tube, and a portion of the continuous multilumen tube is cut away to form the second longitudinal portion.

8. The medical lead of claim 1, further comprising:
a fixation helix disposed on a distal end of the lead body; and
a conductor member disposed in the continuous lumen and electrically coupling the proximal connector to the fixation helix.

9. The medical lead of claim 8, wherein the conductor member is a coiled torque transmission member.

10. The medical lead of claim 8, wherein the proximal connector has a connector body and a terminal pin, wherein a portion of the terminal pin is rotatable with respect to the connector body and wherein a proximal end of the conductor member is coupled to the terminal pin such that torque imparted on the terminal pin is transmitted through the conductor member to the fixation helix.

11. A medical lead comprising:
a multilumen tube defining a first number of lumens along a first longitudinal portion of the tube and a second number of lumens along a second longitudinal portion of the tube, wherein the first number of lumens is larger than the second number of lumens, wherein a continuous lumen extends through both the first and second portions and wherein the wall is substantially continuous through both the first and second longitudinal portions; and
a distal tip portion;
wherein a fluid tight seal is formed between the second portion of the multilumen tube and the distal tip portion, providing a fluid-tight passageway through the first and second portions of the multilumen tube, into the distal tip portion and to the fixation member.

12. The medical lead of claim 11, wherein the wall of the multilumen tube is continuous from the distal end to the proximal end of the multilumen tube.

13. The medical lead of claim 11, wherein the multilumen tube comprises a flexible material and wherein the second longitudinal portion of the multilumen tube is stretched to fit over a portion of the distal tip portion.

14. The medical lead of claim 11, wherein the multilumen tube is continuous through the first longitudinal portion of the tube and the second longitudinal portion of the tube, and a portion of the continuous multilumen tube is cut away to form the second longitudinal portion.

15. The medical lead of claim 11, further comprising:
a fixation helix disposed on a distal end of the lead body; and
a conductor member disposed in the continuous lumen and electrically coupling the proximal connector to the fixation helix.

16. The medical lead of claim 15, wherein the proximal connector has a connector body and a terminal pin, wherein a portion of the terminal pin is rotatable with respect to the connector body and wherein a proximal end of the conductor member is coupled to the terminal pin such that torque imparted on the terminal pin is transmitted through the conductor member to the fixation helix.

17. A medical lead comprising:
a multilumen tube having a distal end and a proximal end and a wall, the wall defining a first number of lumens along a first longitudinal portion of the tube and a second number of lumens along a second longitudinal portion of the tube, wherein a first, continuous lumen extends through both the first and second portions, wherein the wall is substantially continuous through both the first and second longitudinal portions and wherein the first number of lumens is greater than the second number of lumens;
a proximal connector disposed at the proximal end of the medical lead, the proximal connector adapted to connect the lead to an implantable medical device; and
a distal tip portion, the fixation member at least partially disposed within the distal tip portion;
wherein the second portion of the multilumen tube is connected with the distal tip portion, providing a fluid-tight passageway extending through the first and second portions of the multilumen tube and into the distal tip portion.

18. The medical lead of claim 17, wherein the distal tip portion has a distal outer member and a distal inner member disposed within the distal outer member, wherein a space is formed between an outer surface of a proximal portion of the distal inner member and the inner surface of the distal outer member, and wherein the second portion of the multilumen tube is disposed within the space and forms a fluid tight seal with the distal inner member.

19. The medical lead of claim 16, wherein the multilumen tube comprises a flexible material and wherein the second longitudinal portion of the multilumen tube is stretched to fit over a portion of the distal tip portion.

20. The medical lead of claim 19, wherein the material is silicone.

* * * * *